United States Patent [19]
Palmer

[11] Patent Number: 5,500,184
[45] Date of Patent: Mar. 19, 1996

[54] SELF-CONTAINED BIOLOGICAL INDICATORS

[75] Inventor: Steven G. Palmer, Apex, N.C.

[73] Assignee: American Sterilizer Company, Erie, Pa.

[21] Appl. No.: 273,026

[22] Filed: Jul. 8, 1994

Related U.S. Application Data

[63] Continuation of Ser. No. 125,773, Sep. 24, 1993, now U.S. Pat. No. 5,405,580.
[51] Int. Cl.⁶ .............................. A61L 2/00; C12Q 1/22
[52] U.S. Cl. ............................ 422/2; 422/28; 422/56; 422/82.05; 422/119; 435/31; 435/810; 435/287.4; 435/287.6; 206/569
[58] Field of Search .................. 422/2, 28, 119, 422/55, 56, 82.05; 435/31, 291, 296, 299, 300, 810; 206/216, 569

[56] References Cited

U.S. PATENT DOCUMENTS

| | | | |
|---|---|---|---|
| 4,169,123 | 9/1979 | Moore et al. | 422/29 |
| 4,304,869 | 12/1981 | Dyke | 435/296 |
| 4,461,837 | 7/1984 | Karle et al. | 435/299 |
| 4,717,661 | 1/1988 | McCormick et al. | 435/31 |

Primary Examiner—David A. Redding
Attorney, Agent, or Firm—Jones, Day, Reavis & Pogue

[57] ABSTRACT

A biological indicator is disclosed for determining the efficacy of a sterilization cycle using hydrogen peroxide vapor at subatmospheric conditions. The biological indicator includes a vial formed of a substance which resists retention of residual sterilant while also maintaining vial clarity. Also disclosed is an improved cap design which facilitates activation of the biological indicator after the sterilization cycle is complete.

9 Claims, 2 Drawing Sheets

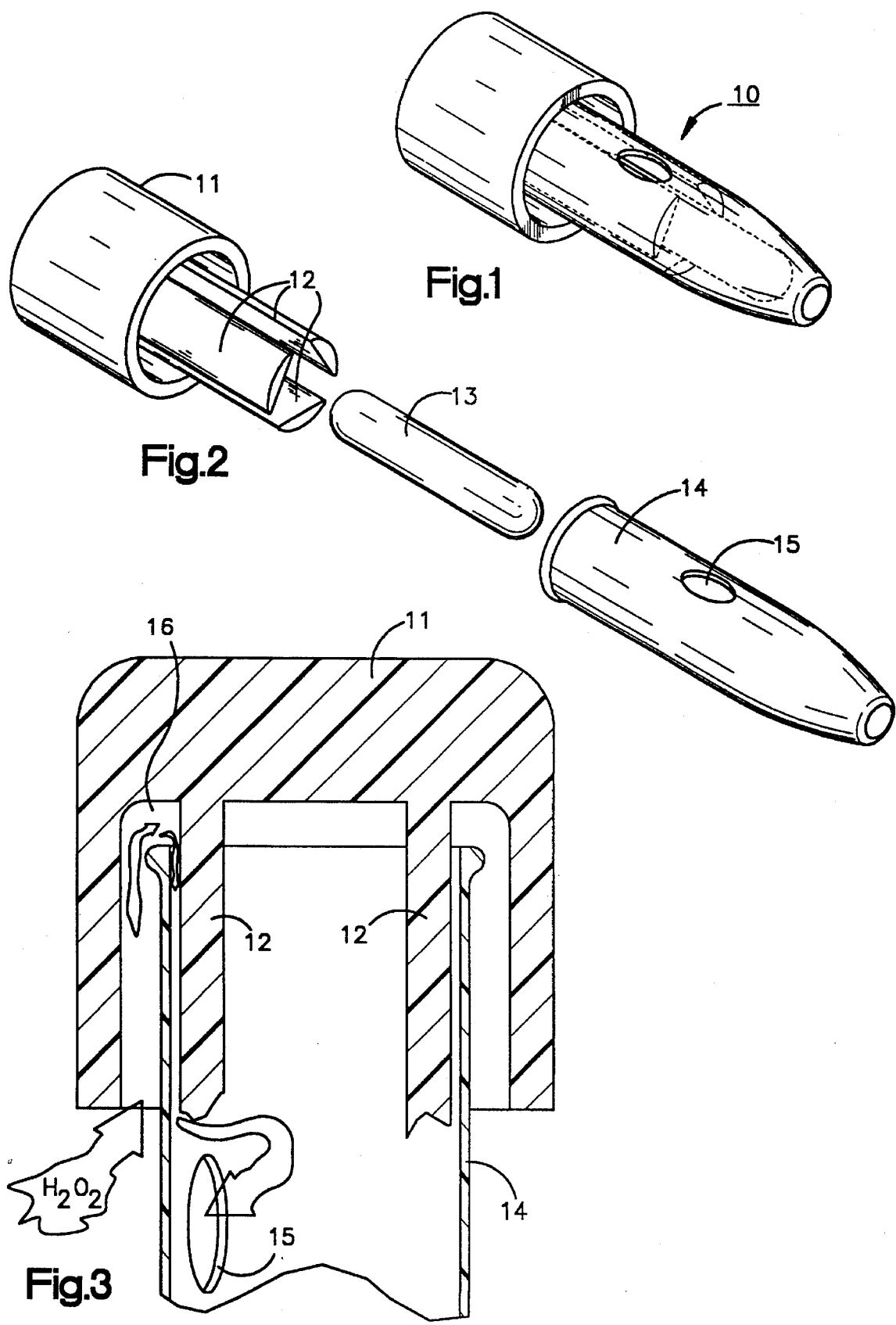

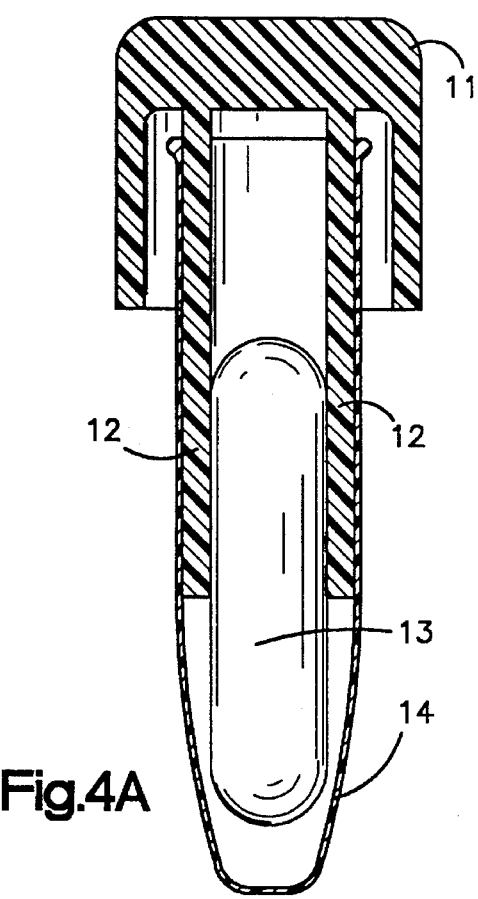 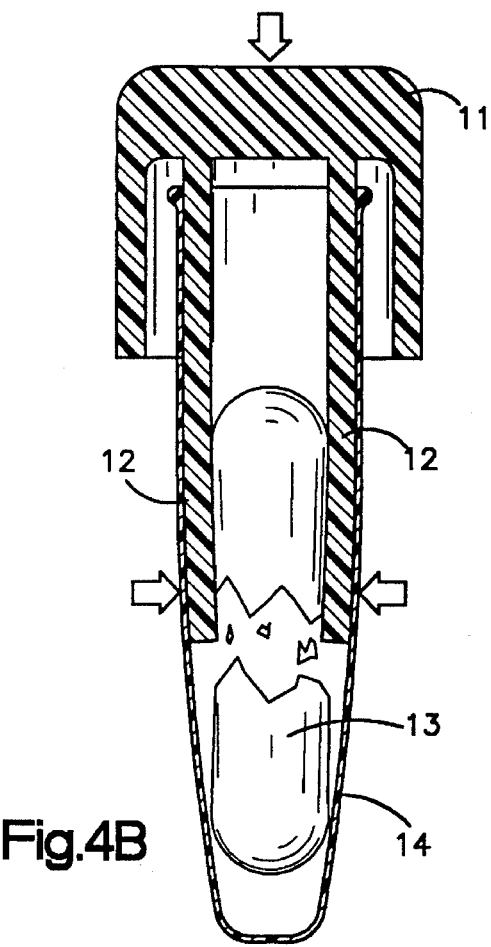
Fig.4A  Fig.4B
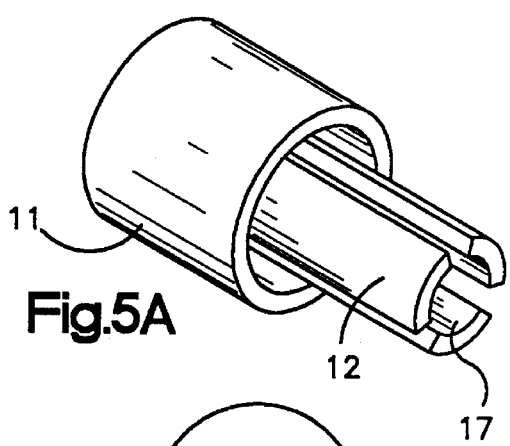 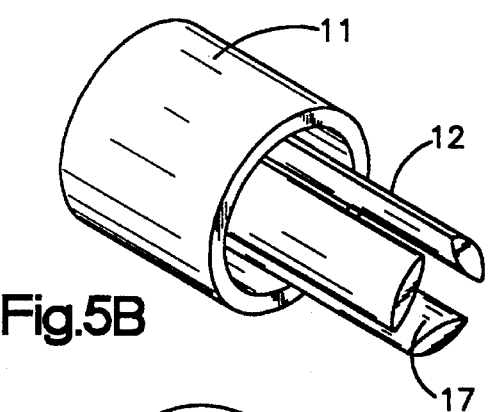
Fig.5A  Fig.5B
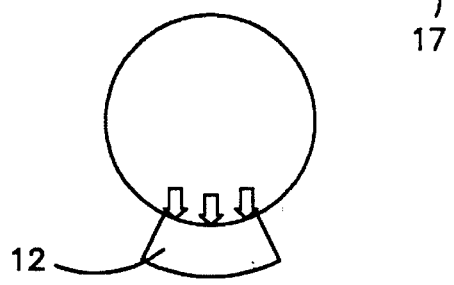 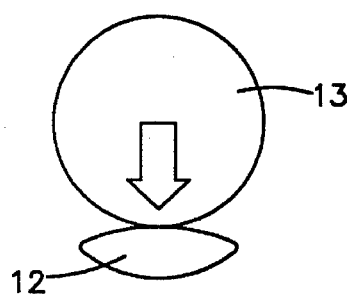
Fig.6A  Fig.6B

SELF-CONTAINED BIOLOGICAL INDICATORS

This is a continuation of copending application Ser. No. 08/125,773, filed on Sep. 24, 1993, now U.S. Pat. No. 5,405,580.

BACKGROUND OF THE INVENTION

In the field of sterilization of articles, it is desirable to insure the quality and integrity of a sterilization environment, and to ensure that a particular load of articles to be sterilized has in fact been exposed to an environment which would have adequately killed bacterial microorganisms. To this end, it is known in the art to provide a "biological indicator", a compact device which insures the efficacy of a sterilization cycle.

Several types of biological indicators are known in the art. Such systems are taught, for example, in U.S. Pat. Nos. 4,304,869 and 4,461,837. These systems offer a self-contained unit which permits a biological sample to be exposed to a sterilizing environment (along with the desired articles to be sterilized), with the unit simultaneously sealing and immersing the biological sample in a growth-inducing medium upon activation of the unit. The growth-inducing medium is mixed with a dye which vividly changes color to indicate spore growth. A color change indicates the presence of spores which suggests that the batch had not been properly sterilized.

In the prior art, the vial is fashioned from polycarbonate, a material which works well in the conventional steam and ethylene oxide sterilization processes. With the advent of hydrogen peroxide vapor systems, it was discovered that the polycarbonate vials did not work well with this sterilant.

In order for typical self-contained biological indicators to be effective, it must be possible to determine the color changes in the growth-inducing medium. In typical devices, the fluid changes color from purple to yellow to indicate contamination.

Hydrogen peroxide sterilization also creates other difficulties. The material used in the spore carrier of the prior art was found to also be incompatible with hydrogen peroxide. Failure of the spore carrier material during a hydrogen peroxide sterilization cycle would yield erroneous results or even total failure of the biological indicator.

In addition, in the prior art, the interior surface of each prong of the cap typically is concave and designed to form around the surface of the ampule. In this configuration, as seen in FIG. 6A, there is substantially complete contact between the prong and ampule and the force of fracture transmitted by the prongs during sealing and activation is spread out over a large area. This structure was discovered to be ineffective with the present invention.

SUMMARY OF THE INVENTION

The present invention overcomes the problems inherent in using conventional biological indicators with hydrogen peroxide based systems. A significant number of inferior outgrowth results were found to be due to a raw material incompatibility which resulted in significant residual levels of hydrogen peroxide adhering to the polycarbonate vial. Such residual peroxide could injure or continue to kill remaining spores or inhibit their outgrowth in the biological indicator after the predetermined sterilization cycle has been completed and after the product has been removed from the sterilizer. According to the present invention, there is provided a biological indicator having microorganisms and a growth medium contained in a capped vial constructed of clear polypropylene. The inventors have discovered that clear polypropylene provides particularly good performance and retains a low level of residual hydrogen peroxide as compared to other materials available for use as a vial. In combination with this good performance, the present vial material is also substantially transparent, and thus offers good "clarity", permitting more precise determination of the color change pointing to non-sterile conditions.

The present invention also provides a spore carrier made of ultrafine glass fibers in an acrylic binder which has been found to be inert to attack from hydrogen peroxide and the chosen bacteriological spores. Thus, the spore carrier according to the present invention will not fail during use.

The prongs of the present invention are configured to provide line contact with the ampule. This structural feature has been found most advantageous for ampule activation, as used with a polypropylene vial.

The foregoing operation and configuration, along with the other features and advantages of the present invention may be realized and obtained by the following detailed description, the accompanying drawings and the appended claims.

BRIEF DESCRIPTION OF THE DRAWINGS

FIG. 1 is a general view showing the biological indicator;

FIG. 2 is an exploded assembly view showing the components of the biological indicator;

FIG. 3 is a sectional view illustrating the manner with which sterilant is admitted into the biological indicator;

FIGS. 4A and 4B show the activation of the biological indicator after the sterilization cycle;

FIGS. 5A and 5B are oblique views comparing the caps of the prior art and the preferred embodiment showing differences in the prongs; and FIGS. 6A and 6B are cross-sectional views comparing the performance of the caps of the prior art and the preferred embodiment.

DETAILED DESCRIPTION OF THE PREFERRED EMBODIMENTS

Referring now to FIGS. 1 and 2, the preferred embodiment of the present biological indicator 10 essentially includes a cap 11 with three flexibly projecting "prongs" 12 which are configured to substantially surround and contact an ampule 13 of growth-inducing medium. The cap 11 and ampule 13 are then fitted inside a vial 14 into which is also inserted a spore carrier 15. During activation of the device, the prongs 12 are forced against the ampule 13, thus fracturing it and releasing the growth-inducing medium.

The spore carrier substrate typically is inoculated with an approximately $10^4$ population of spores of a known strain of *Bacillus stearothermophilus* (*B.st.*). The combination of the spore sample and the vial/cap assembly medium mimics the resistance of a $1 \times 10^6$ population of *B.st.* on a stainless steel carrier when subjected to hydrogen peroxide vapor sterilant at less than atmospheric pressure.

The biological indicator 10 is designed to admit hydrogen peroxide sterilant vapor onto the spore carrier 15 as shown in regard to FIG. 3. In the inactivated state, the cap 11 is configured on the vial 14 in such a way as to permit vapor/gas between the interior of the vial and the outside environment.

During sterilization, hydrogen peroxide vapor can enter the vial chamber by way of a "tortuous path" 16 whereby the vapor must negotiate at least two 90° bends in order to enter the vial. The sterilant entering the chamber then acts upon the spore carrier 15 in order to expose the carrier to the same environment encountered by the other articles to be sterilized.

Upon completion of the sterilization cycle, the biological indicator 10 is removed from the sterilizer and thereby is exposed to a non-sterile environment which may contain airborne microorganisms. Because there will be little or no pressure differential between the exterior and the interior of the container 10, there is minimal or extremely low probability that the non-sterile environment, e.g. air, will flow into the chamber of the vial 14, carrying with it airborne microorganisms. Access to the chamber of the vial 14 by airborne microorganisms may be gained only if the microorganisms negotiate the tortuous path 16. Such migration will be unlikely to occur because the microorganisms are incapable of independent movement and must be carried along by any negligible air currents that would traverse the tortuous path.

After being sterilized with the desired articles in the manner described above, the biological indicator is activated as shown in FIGS. 4A and 4B. The top of the cap 11 is pressed down, sealing the top of the vial 14, cutting off further vapor transmission. As the cap 11 is pressed down, the prongs 12 are pushed into the taper of the vial 14, which forcibly crush the ampule 13, releasing the growth-inducing medium upon the spore carrier 15. Should any viable spores remain (i.e. should the sterilization cycle be inadequate), they will thrive on the growth-inducing medium in the sealed vial 14. Should spore growth occur, the dye in the growth-inducing medium will vividly change color in response to well known biochemical reactions produced by *B.st.*

The present invention addresses the need to ensure accurate test results while at the same time offering sufficient "clarity" and abrasion resistance, including resistance to nicks, scratches and peeling. Polycarbonate was found to contain a high level of residual hydrogen peroxide which affects the accuracy of a sterilization test. In seeking to replace polycarbonate, several different vial materials were first selected for a desired level of clarity, including polymers from the group acrylic, polypropylene and modified styrene such as styrene-butadiene copolymer, sold under the trade name "KR03" by Phillips 66 Company. Vials wee formed from the selected materials using the standard techniques of injection molding. A Minimum Inhibitory Concentration (MIC) test was performed and it was determined that a concentration of residual hydrogen peroxide of 40 μg/ml which would permit an acceptable outgrowth of *B.st.* after a desired interval.

The steps of the MIC test are as follows: A growth promotion test was performed. A study sample of these vials was run through a hydrogen peroxide sterilization cycle. At the end of this cycle, a sample containing a standard quantity of *B.st.* spores was injected into each vial. The vials were then maintained at an incubation temperature of 55°–60° C. At the end of 48 hours, the outgrowth of *B.st.* spores was observed. It was concluded that spore samples having residual hydrogen peroxide in solution at an initial concentration of less than 40 μg/ml would grow out to the desired level within 48 hours. Samples having higher levels would display inhibited outgrowth and would not grow out as quickly, thus offering inconclusive sterility results. Polycarbonate had a higher level and did not grow out for 72 hours due to the levels of residual hydrogen peroxide. After processing through an extended cycle, initial levels of hydrogen peroxide in solution with the spore sample were measured by subjecting the sample to a variation of the Xylenol Orange Spectrophotometric test for measuring low concentrations of hydrogen peroxide, such techniques being known in the art.

Upon completing this growth promotion test, it was observed that the modified styrene materials had residual hydrogen peroxide concentrations under the acceptable level of 40 μg/ml, and thus displayed desirable outgrowth after 48 hours. However, these materials scratched easily and thus are not the preferred embodiment. Acrylic had an acceptable abrasion resistance, but had a high level of residuals.

It was found that clear polypropylene (in the preferred embodiment, Exxon Escorene 1105) was found to offer significantly better results than the prior art polycarbonate. This variety of polypropylene has been found to successfully meet all three criteria: clarity, abrasion resistance and low residual level.

The reason that polypropylene performs unusually well for this application is not fully understood. Presumably it is a function of the molecular structure of polypropylene. In the preexisting prior art biological indicators, the caps 11 had been made of opaque polypropylene and so the desirable resistance to hydrogen peroxide is realized without replacing the existing cap material.

On a molecular level, polypropylene has a very linear polymer chain. The sidechains of this polymer have a very low molecular weight, especially as compared to polycarbonate which has large sidechains of relatively high molecular weight. These sidechains are believed to promote the retention of hydrogen peroxide, and thus produce the high levels of residuals that have been observed.

In addition to its providing resistance to the hydrogen peroxide sterilant, the Exxon Escorene 1105 clear polypropylene also was chosen for being less opaque, thus improving the accuracy of test results. Ordinary polypropylene suffers from being somewhat "cloudy." Escorene 1105 contains additives that improve its clarity. Using this type of clear polypropylene, clarity is significantly improved and consequently, accurate monitoring of hydrogen peroxide sterilization cycles is facilitated, with the result that "false positive" test results can be reduced considerably. Polypropylene also works well in injection molding equipment, being of a sufficiently low viscosity that it is easily molded.

While the discovery of the hydrogen peroxide resistance of polypropylene is most applicable in the present solution to the problem with biological indicator vials, it is contemplated that this material's properties may be exploited in other applications adapted for use in hydrogen peroxide systems. For example, worker safety is always a concern and hydrogen peroxide is a well-known corrosive material. It may be useful to form the components of a variety of implements from polypropylene in order to protect workers from exposure risk. Such implements include personnel monitoring systems as are known in the art.

Another application is the use of polypropylene elements in a "biological challenge test" a kit which includes the general elements of a biological indicator, and which simulates a "worst case" contaminated load, thus insuring the overall efficacy of a sterilization cycle. Polypropylene also makes a suitable packaging "barrier film", used as a cover layer for the articles inserted into a "heat seal" pouch which is placed in a sterilizer unit as known in the art.

Referring now to FIG. 5B, the design of the prongs 12 is also part of the present invention. Polypropylene has been found to be problematic using prior art structures because it is somewhat less rigid than the prior art polycarbonate. Even Exxon Escorene 1105, with its improved mechanical strength, does not provide rigidity equal to polycarbonate. The vials of the present invention tend to deform upon application of the activation force while using caps with the conventional prongs. This deformation necessitates a very large application of force upon the cap 11 in order to fracture the ampule 13.

As shown in FIG. 6B, this problem is overcome in the present invention by configuring the interior surfaces 17 of the prongs 12 to contact the ampule 13 over a minimal area. In the preferred embodiment, these are convex in shape. Upon activation, greater pressure is exerted upon the ampule 13 as the force is more concentrated onto a smaller area. As a result, the ampule fractures more easily and at a smaller application of force, thus facilitating activation without deforming the polypropylene vials.

The spore carrier 15, according to the present invention, is formed from a composite of an ultrafine glass fiber material in an acrylic binder, of the type used in solution filtration systems. It has been discovered that this composite offers high chemical resistance to the hydrogen peroxide sterilant and provides a stable substrate for the *B.st.* spores. Consequently, failures of the spore carrier 15 are greatly diminished.

The foregoing description of the preferred embodiment has been presented for purposes of illustration and description. It is not intended to be limiting insofar as to exclude other modifications and variations such as would occur to those skilled in the art. Any modifications or variations such as would occur to those skilled in the art in view of the above teaching are contemplated as being within the scope of the invention.

What is claimed is:

1. A biological indicating system for use in sterilization processes comprising:

a biological indicator, including biological matter which is exposed to a sterilant comprising hydrogen peroxide and further including an indicating medium used to detect the presence of viable biological matter after exposure to said sterilant, said biological matter being retained on a carrier substrate formed of a first predetermined material of ultrafine glass fibers in an acrylic binder;

a vial for retaining and holding said biological indicator, said vial is formed of a second predetermined material selected to maintain hydrogen peroxide eterilant residue at a desired low level while at the same time providing clarity, whereby said hydrogen peroxide sterilant residue level is sufficiently low to substantially avoid erroneous biological detection results;

a cap which cooperates with said vial to admit said sterilant into said biological indicator.

2. The biological indicating system as recited in claim 1 wherein:

said second predetermined material comprises polypropylene.

3. The biological indicating system as recited in claim 1 wherein:

said second predetermined material consists essentially of polypropylene.

4. A biological indicating system for use in sterilization processes comprising:

a biological indicator, including biological matter retained on a carrier substrate formed of a first predetermined material of ultrafine glass fibers in an acrylic binder, said biological matter being exposed to a sterilant comprising hydrogen peroxide said biological indicator further including an indicating medium which is contained in an ampule and is used to detect the presence of viable biological matter after exposure to said sterilant;

a vial for retaining and holding said biological indicator, said vial is formed of a second predetermined material selected to maintain hydrogen peroxide sterilant residue at a sufficiently low level to substantially avoid erroneous biological detection results while at the same time providing clarity;

a cap which cooperates with said vial to admit said sterilant and alternatively to seal and activate said biological indicator, wherein said cap further comprises:

a plurality of flexible projections depending from said cap and constructed to wedge between the ampule and the vial and thereby fracture said ampule as said cap is moved from a first position to a second position;

wherein a surface upon the interior of each of said flexible projections is configured such that the surface makes minimal contact with said ampule, and is further configured so that when said cap is moved from said first position to said second position, the force is placed upon a small area of said ampule, facilitating the fracture thereof.

5. The biological indicating system as recited in claim 4 wherein:

said second predetermined material comprises polypropylene.

6. The biological indicating system as recited in claim 4 wherein:

said second predetermined material consists essentially of polypropylene.

7. A method of minimizing contamination by residuals in hydrogen peroxide processes, said method including the steps providing a sterilization treatment process utilizing a sterilant comprising hydrogen peroxide;

providing a biological indicator including an element formed of a predetermined material wherein said predetermined material retains hydrogen peroxide residue at a sufficiently low level to substantially avoid erroneous biological detection results;

carrying out said sterilization treatment process using said biological indicator.

8. The method as recited in claim 7 wherein the predetermined material comprises a polymer selected from the group polyethylene, polystyrene and polypropylene.

9. The method as recited in claim 7 wherein the predetermined material consists essentially of polypropylene.

* * * * *